United States Patent
Steinke et al.

(10) Patent No.: US 11,648,403 B2
(45) Date of Patent: *May 16, 2023

(54) MANAGEMENT OF STIMULATION SAFETY LIMITS IN A NEUROSTIMULATION SYSTEM

(71) Applicant: Boston Scientific Neuromodulation Corporation, Valencia, CA (US)

(72) Inventors: Gustav Karl Steinke, Valencia, CA (US); Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 200 days.

This patent is subject to a terminal disclaimer.

(21) Appl. No.: 17/170,503

(22) Filed: Feb. 8, 2021

(65) Prior Publication Data

US 2021/0154479 A1    May 27, 2021

Related U.S. Application Data

(63) Continuation of application No. 16/284,856, filed on Feb. 25, 2019, now Pat. No. 10,960,212, which is a
(Continued)

(51) Int. Cl.
*A61N 1/36* (2006.01)
*A61N 1/372* (2006.01)

(52) U.S. Cl.
CPC ....... *A61N 1/36142* (2013.01); *A61N 1/3605* (2013.01); *A61N 1/36071* (2013.01); *A61N 1/36146* (2013.01); *A61N 1/37235* (2013.01)

(58) Field of Classification Search
CPC ................................................. A61N 1/36142
(Continued)

(56) References Cited

U.S. PATENT DOCUMENTS

| 6,052,624 | A | 4/2000 | Mann |
| 6,516,227 | B1 | 2/2003 | Meadows et al. |

(Continued)

OTHER PUBLICATIONS

International Preliminary Report on Patentability issued in PCT/US2014/032865, dated Oct. 15, 2015.
(Continued)

*Primary Examiner* — Nicole F Lavert
(74) *Attorney, Agent, or Firm* — Branch Partners PLLC; Bruce E. Black

(57) ABSTRACT

An electrical stimulation system for use with a plurality of electrodes implanted within a tissue region comprises a neurostimulator configured for delivering electrical stimulation energy to the plurality of electrodes in accordance with a set of stimulation parameters, thereby injecting a charge into the tissue region, a control device configured for receiving user input to modify the set of stimulation parameters, and controller/processor circuitry configured for, in response to the user input computing a charge injection metric value as a function of a physical electrode parameter and an electrical source parameter for a first set of the electrodes, wherein the electrode set comprises at least two electrodes, comparing the computed charge injection metric value to a safety threshold value, and performing a corrective action based on the comparison.

20 Claims, 9 Drawing Sheets

Related U.S. Application Data continuation of application No. 15/955,453, filed on Apr. 17, 2018, now Pat. No. 10,258,799, which is a continuation of application No. 15/651,578, filed on Jul. 17, 2017, now Pat. No. 9,974,960, which is a continuation of application No. 15/168,511, filed on May 31, 2016, now Pat. No. 9,744,362, which is a continuation of application No. 14/244,652, filed on Apr. 3, 2014, now Pat. No. 9,358,394.

(60) Provisional application No. 61/808,224, filed on Apr. 4, 2013.

(58) Field of Classification Search
USPC .......................................................... 607/59
See application file for complete search history.

(56) References Cited

U.S. PATENT DOCUMENTS

| | | | |
|---|---|---|---|
| 6,845,267 | B2 | 1/2005 | Harrison et al. |
| 6,895,280 | B2 | 5/2005 | Meadows et al. |
| 6,950,707 | B2 | 9/2005 | Whitehurst |
| 6,993,384 | B2 | 1/2006 | Bradley et al. |
| 7,650,184 | B2 | 1/2010 | Walter |
| 7,801,600 | B1 | 9/2010 | Carbunaru et al. |
| 8,019,439 | B2 | 9/2011 | Kuzma et al. |
| 2010/0010566 | A1 | 1/2010 | Thacker et al. |
| 2010/0121409 | A1 | 5/2010 | Kothandaraman et al. |
| 2011/0313488 | A1 | 12/2011 | Hincapie Ordonez et al. |
| 2012/0290038 | A1 | 11/2012 | Moffitt et al. |
| 2012/0290039 | A1 | 11/2012 | Moffitt et al. |
| 2012/0290040 | A1* | 11/2012 | Moffitt ............... A61N 1/37241 607/45 |

OTHER PUBLICATIONS

PCT International Search Report for PCT/US2014/032865, Applicant: Boston Scientific Neuromodulation Corporation, Form PCT/ISA/210 and 220, Docket No. 12-0379W001, dated Aug. 14, 2014.

CT Written Opinion of the International Search Authority for PCT/US2014/032865, Applicant: Boston Scientific Neuromodulation Corporation, Form PCT/ISA/237, Docket No. 12-0379W001, dated Aug. 14, 2014.

Shannon, RV, A Model of Safe Levels for Electrical Stimulation, IEEE-TBME, vol. 39, No. 4, pp. 424-426, Apr. 1992.

Official Communication for U.S. Appl. No. 15/168,511 dated Dec. 28, 2016.

Official Communication for U.S. Appl. No. 14/244,652 dated Sep. 21, 2015.

Official Communication for U.S. Appl. No. 15/651,578 dated Dec. 18, 2017.

Official Communication for U.S. Appl. No. 15/955,453 dated Jul. 13, 2018.

Official Communication for U.S. Appl. No. 16/284,856 dated Jun. 25, 2020.

* cited by examiner

| Surface Area (cm²) | 0.015 | 0.015 | 0.015 | 0.015 | | |
|---|---|---|---|---|---|---|
| | e1 | e2 | e3 | e4 | k2 | k (original) |
| 1 | 100% | 0% | 0% | 0% | 1.50 | 1.50 |
| 2 | 90% | 10% | 0% | 0% | 1.42 | |
| 3 | 80% | 20% | 0% | 0% | 1.33 | |
| 4 | 70% | 30% | 0% | 0% | 1.27 | |
| 5 | 60% | 40% | 0% | 0% | 1.22 | |
| 6 | 50% | 50% | 0% | 0% | 1.20 | 1.20 |
| 7 | 40% | 60% | 0% | 0% | 1.22 | |
| 8 | 30% | 70% | 0% | 0% | 1.27 | |
| 9 | 20% | 80% | 0% | 0% | 1.33 | |
| 10 | 10% | 90% | 0% | 0% | 1.42 | |
| 11 | 0% | 100% | 0% | 0% | 1.50 | 1.50 |

| Surface Area (cm²) | 0.015 | 0.06 | 0.015 | 0.015 | | |
|---|---|---|---|---|---|---|
| | e1 | e2 | e3 | e4 | k2 | k (original) |
| 1 | 100% | 0% | 0% | 0% | 1.50 | 1.50 |
| 2 | 90% | 10% | 0% | 0% | 1.41 | |
| 3 | 80% | 20% | 0% | 0% | 1.31 | |
| 4 | 70% | 30% | 0% | 0% | 1.21 | |
| 5 | 60% | 40% | 0% | 0% | 1.10 | |
| 6 | 50% | 50% | 0% | 0% | 1.00 | |
| 7 | 40% | 60% | 0% | 0% | 0.90 | |
| 8 | 30% | 70% | 0% | 0% | 0.83 | |
| 9 | 20% | 80% | 0% | 0% | 0.80 | 0.80 |
| 10 | 10% | 90% | 0% | 0% | 0.83 | |
| 11 | 0% | 100% | 0% | 0% | 0.90 | 0.90 |

| Surface Area (cm²) | 0.015 | 0.015 | 0.015 | 0.015 | | |
|---|---|---|---|---|---|---|
| | e1 | e2 | e3 | e4 | k2 | k (original) |
| 1 | 33% | 33% | 33% | 0% | 1.02 | 1.02 |
| 2 | 40% | 33% | 27% | 0% | 1.04 | |
| 3 | 50% | 33% | 17% | 0% | 1.09 | |
| 4 | 60% | 33% | 7% | 0% | 1.18 | |
| 5 | 67% | 33% | 0% | 0% | 1.25 | |

| Surface Area (cm²) | 0.03 | 0.015 | 0.015 | 0.015 | | |
|---|---|---|---|---|---|---|
| | e1 | e2 | e3 | e4 | k2 | k (original) |
| 1 | 33% | 33% | 33% | 0% | 0.95 | |
| 2 | 33% | 40% | 27% | 0% | 0.96 | |
| 3 | 33% | 50% | 17% | 0% | 1.02 | |
| 4 | 33% | 60% | 7% | 0% | 1.12 | |
| 5 | 33% | 67% | 0% | 0% | 1.20 | |
| 6 | 33% | 60% | 7% | 0% | 1.12 | |
| 7 | 33% | 50% | 17% | 0% | 1.02 | |
| 8 | 33% | 40% | 27% | 0% | 0.96 | |
| 9 | 33% | 33% | 33% | 0% | 0.95 | |
| 10 | 40% | 33% | 27% | 0% | 0.92 | |
| 11 | 50% | 33% | 17% | 0% | 0.92 | |
| 12 | 50% | 25% | 25% | 0% | 0.90 | 0.90 |
| 13 | 50% | 33% | 17% | 0% | 0.92 | |
| 14 | 60% | 33% | 7% | 0% | 0.97 | |
| 15 | 67% | 33% | 0% | 0% | 1.02 | 1.02 |

| e1 | e2 | e3 | e4 | e5 | e6 | e7 | e8 |
|---|---|---|---|---|---|---|---|
| 0.2 | 0.6 | 1.0 | 0.6 | 0.2 | 0.0 | 0.0 | 0.0 |

FIG. 9a

| e1 | e2 | e3 | e4 | e5 | e6 | e7 | e8 |
|---|---|---|---|---|---|---|---|
| 0.0 | 0.0 | 0.0 | 0.0 | 0.0 | 0.6 | 1.0 | 0.6 |

FIG. 9b

MANAGEMENT OF STIMULATION SAFETY LIMITS IN A NEUROSTIMULATION SYSTEM

CROSS-REFERENCE TO RELATED APPLICATION

This application is a continuation of U.S. application Ser. No. 16/284,856, filed Feb. 25, 2019, which is a continuation of U.S. application Ser. No. 15/955,453, filed Apr. 17, 2018, which issued as U.S. Pat. No. 10,258,799, which is a continuation of U.S. application Ser. No. 15/651,578, filed Jul. 17, 2017, which issued as U.S. Pat. No. 9,974,960, which is a continuation of U.S. application Ser. No. 15/168,511, filed May 31, 2016, which issued as U.S. Pat. No. 9,744,362, which is a continuation of U.S. application Ser. No. 14/244,652, filed Apr. 3, 2014, which issued as U.S. Pat. No. 9,358,394, which claims priority to Provisional Application No. 61/808,224, filed Apr. 4, 2013, all of which are herein incorporated by reference in their entirety.

TECHNICAL FIELD

The present invention relates to management of stimulation safety limits, and more particularly, to management of tissue safety limits in a neurostimulation system having more than one electrode.

BACKGROUND

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation. More pertinent to the present inventions described herein, Deep Brain Stimulation (DBS) has been applied therapeutically for well over a decade for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707, which are expressly incorporated herein by reference.

Each of these implantable neurostimulation systems typically includes one or more electrode carrying stimulation leads, which are implanted at the desired stimulation site, and a neurostimulator implanted remotely from the stimulation site, but coupled either directly to the neurostimulation lead(s) or indirectly to the neurostimulation lead(s) via a lead extension. A single stimulation lead may contain electrodes of different sizes. The neurostimulation system may further comprise a handheld external control device to remotely instruct the neurostimulator to generate electrical stimulation pulses in accordance with selected electrical stimulation parameters.

Electrical stimulation energy may be delivered from the neurostimulator to the electrodes in the form of an electrical pulsed waveform. Thus, the stimulation energy may be controllably delivered to the electrodes to stimulate the tissue. The set of electrodes, including those on and off the lead, used to deliver the electrical pulses to the targeted tissue constitutes an electrode set, with the electrodes capable of being selectively programmed to act as anodes (positive), cathodes (negative), and/or left off (zero). In other words, an electrode set represents the polarity being positive, negative, or zero. Other parameters that may be controlled or varied include, but are not limited to, the amplitude, width, rate, regularity, and ramp of the electrical pulses provided through the electrode array. Each electrode set, along with its electrical pulse parameters, can be referred to as a "stimulation parameter set."

With some neurostimulation systems, and in particular, those with independently controlled current and/or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e. fractionalized electrode sets).

As briefly discussed above, an external control device can be used to instruct the neurostimulator to generate electrical stimulation pulses in accordance with selected stimulation parameters. Typically, the stimulation parameters programmed into the neurostimulator can be adjusted by the user by manipulating controls on the external user control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate, activate, or affect a volume of tissue in accordance with the set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the amount of non-target tissue that is stimulated. A typical stimulation parameter set may include the electrodes that acting as anodes or cathodes, as well as the amplitude, duration, and rate of the stimulation pulses.

To facilitate the selection of the stimulation parameters, the clinician generally programs the external control device, and if applicable the neurostimulator, through a computerized programming system. This programming system can be a self-contained hardware/software system, or can be defined predominately by software that is run on a standard personal computer (PC). The PC or custom hardware may actively control the characteristics of the electrical stimulation generated by the neurostimulator to allow the optimum stimulation parameters to be determined based on patient feedback, or other means, and to subsequently program the external control device with the optimum electrical stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external control device, and if applicable the neurostimulator, with a set of stimulation parameters that best addresses the disorder or painful site.

Significantly, there are limits to how much charge (both in terms of total charge per pulse (or phase) and charge density per pulse) can be injected into tissue using one manner (e.g. biphasic, charge-balanced waveforms) without causing cell trauma and/or electrochemical damage (i.e., corrosion) to the electrodes. Each electrode, depending upon its physical properties (which include, but are not limited to, its size, shape, material, surface characteristics, and/or state), has a charge threshold level (which may also be affected by implant location, adjacent tissue type, and other biological factors) that should not be exceeded to ensure that the amount of charge applied to the electrode will not cause irreparable electrochemical harm to the electrode or induce cellular trauma. Smaller sized electrodes generally have lower charge threshold levels than larger sized electrodes that are manufactured of the same material because the smaller sized electrodes have higher charge densities.

Thus, with regard to tissue safety, both total charge and charge density have been taken into account to avoid cell trauma. As such, the Shannon model, which accounts for a single electrode of a surface area "A" through which a charge amount "Q" is injected, was created in 1992 for evaluating tissue safety limits. In particular, the Shannon model calculates a k-value in accordance with the equation:

$$k = \log_{10}\left(\frac{Q}{A}\right) + \log_{10}(Q) = \log_{10}\left(\frac{Q^2}{A}\right). \quad [1]$$

(See Shannon, R. V., A Model of Safe Levels for Electrical Stimulation, IEEE-TBME, Vol. 39, No. 4, pp. 424-426, April 1992). It should be appreciated that the value of k comprises two terms: the log of the charge density, and the log of the charge. The author proposed that a tissue safety limit of k equal to 1.5 or lower should be maintained to ensure tissue safety given the assumptions listed in the publication.

Management of charge injection for safe stimulation in commercial stimulators today is performed using one variable (charge density) on an electrode-by-electrode basis. This approach is sufficient for present-day stimulation systems and electrode surface areas, because side-effects prohibit a clinician from practically reaching a tissue safety limit. In particular, a patient undergoing neurostimulation therapy would be expected to exhibit side effects well before cell trauma would occur. The onset of side-effects is primarily caused by the total charge per pulse, thereby naturally limiting the total charge per pulse (as well as the charge density per pulse) that can be applied to the patient. Due to the relatively large area, and resulting low charge density, of prior art electrodes, the charge density per pulse is also naturally limited by the side-effects experienced by the patient.

While managing charge injection for safe stimulation based on the charge density for each electrode may be acceptable for conventional neurostimulation systems, such charge injection management does not adhere to the Shannon model. For example, if electrical current at 450 µs and 4 mA is delivered to a single active electrode having a surface area of 0.06 cm², the charge, charge density, and k-value are 1.8 µs, 30 µC/cm², and 1.73, respectively. If the amplitude of the electrical current is doubled to 8 mA, and the surface area of the electrode is doubled to 0.12 cm², the charge-density remains the same (30 µC/cm²), but the k-value increases substantially to 2.03. This example shows that a charge-density limit alone does not manage the k-value, and can result in breaches of a k-value threshold designed for one electrode.

Although conformance with the Shannon model may not be necessary when an electrode is relatively large, as the size of electrodes becomes smaller (e.g., the use of segmented electrodes is becoming prevalent in the context of DBS), thereby effectively increasing the charge density per pulse, it may be possible to cause cell trauma before the onset of side-effects. Therefore, an improved charge management solution is needed as new leads are developed with smaller electrodes and side-effects cannot be relied on to naturally manage adherence to the Shannon model.

It is possible that for a case of multiple active electrodes, an approach that relies on the Shannon model (or a surrogate parameter for k, such as charge-density or charge as a function of surface area), but which replaces the electrode surface area with a cumulative or effective contact surface area (e.g., could be a sum of active electrode surface areas or the sum of active electrode surface areas multiplied by a dispersion factor greater than 1 to get credit for the expanded spatial distribution) could be used. Such an approach, which is in essence a reduction of the problem to the Shannon model, seems reasonable for the case where a single electrical source is used and all active electrodes (of the same polarity) are at the same potential. However, use of independent electrical sources (e.g., like multiple independent current control (MICC) devices) can create distributions of currents that are not readily reduced to the Shannon model, and a new approach is needed.

SUMMARY

In accordance with the present invention, a neurostimulation system for use with a plurality of electrodes implanted within a tissue region is provided. The neurostimulation system comprises a neurostimulator (which may be implantable) configured for delivering electrical stimulation energy to the plurality of electrodes in accordance with a set of stimulation parameters, thereby injecting a charge into the tissue region. The neurostimulation device further comprises a control device configured for receiving user input to modify the stimulation parameter set, and controller/processor circuitry, which may be, e.g., contained in the control device, the neurostimulator, or both. The control device may be an external control device, or alternatively, an internal control device separate from the IPG.

The controller/processor circuitry is configured for, in response to the user input, computing a charge injection metric value as a function of a physical electrode parameter (e.g., at least one of an electrode surface area, an electrode surface shape, and an electrode material) and an electrical source parameter (e.g., at least one of a current, a voltage, a charge, charge density, and an impedance) for a set of the electrodes, wherein the electrode set comprises at least two electrodes, comparing the computed charge injection metric value to a safety threshold value, and performing a corrective action based on the comparison.

The corrective action may, e.g., comprise preventing the neurostimulation device from delivering the electrical stimulation energy to the plurality of electrodes. Or the corrective action may, e.g., comprise delivering the electrical stimulation energy to the electrode set in accordance with a different set of stimulation parameters. Or the corrective action may, e.g., comprise directing the control device to convey an warning signal to the user.

In one embodiment, the controller/processor circuitry is configured for directing the neurostimulator to deliver the electrical stimulation energy to the plurality of electrodes in accordance with the modified stimulation parameter set if the computed charge injection metric value does not breach the threshold charge injection metric value, and performing the corrective action if the computed charge injection metric value breaches the threshold charge injection metric value.

If the physical electrode parameter is an electrode surface area, and the electrical source parameter is a charge, the ratios between the injected charge and the surface area for at least two of the electrodes may be different. The tissue charge injection safety value may be computed in accordance with the equation $$k2 = \left( \log_{10} \sum_{i=1}^{n} \frac{Q_i^2}{A_i} \right),$$

where k2 is the tissue charge injection safety value, i is an electrode designator, n is the number of electrodes, $Q_i$ is the charge injected by the electrode i, and $A_i$ is the surface area of the electrode i. Or the tissue charge injection safety value may be computed in accordance with the equation $$k2 = \left( \log_{10} \sum_{i=1}^{n} W_i \frac{Q_i^2}{A_i} \right),$$

where k2 is the tissue charge injection safety value, i is an electrode designator, n is the number of electrodes, $Q_i$ is the charge injected by the electrode i, $A_i$ is the surface area of the electrode i, and Wi is a weighting value for the electrode i. The weighting value $W_i$ may be, e.g., a binary value or a graduated value. In one embodiment, the controller/processor circuitry is configured for determining the weighting value $W_i$ for each electrode in the electrode set based on an adjacency of the respective electrode relative to a reference electrode in the electrode set. In another embodiment, the controller/processor circuitry is configured for determining the weighting value $W_i$ for each electrode in the electrode set based on a polarity of the respective electrode. In another embodiment, $W_i$ may depend on another system parameter, e.g. rate, or maximum instantaneous rate.

The neurostimulation system may further comprise memory storing a plurality of different safety threshold values, in which case, the controller/processor circuitry may be configured for selecting the safety threshold value from the different safety threshold values based on a characteristic (e.g., the same frequency or the same polarity) shared by the electrode set In an optional embodiment, multiple k2-values may be computed for different sets of electrodes. In this case, the controller/processor circuitry may be configured for, in response to the user input, computing at least one other charge injection metric value as a function of a physical electrode parameter and an electrical source parameter for each of at least one other set of the electrodes. Each of the set of electrodes and the other electrode(s) are different from each other, and each of the other electrode set(s) comprises at least two electrodes. The controller/processor circuitry may be further configured for comparing a function (e.g., a maximum, a sum, an average, or a minimum) of the computed charge injection metric value and the at least one other computed charge injection metric value to the safety threshold value, and performing the corrective action based on the computed function.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which:

FIG. 5a is a table illustrating k2-values and original k-values computed for different electrical current distributions between two electrodes of the same size;

FIG. 5b is a diagram of the computed k2-values and original k-values of the table in FIG. 5a;

FIG. 6a is a table illustrating k2-values and original k-values computed for different electrical current distributions between two electrodes of different sizes;

FIG. 6b is a diagram of the computed k2-values and original k-values of the table in FIG. 6a;

FIG. 7a is a table illustrating k2-values and original k-values computed for different electrical current distributions between three electrodes of the same size;

FIG. 7b is a diagram of the computed k2-values and original k-values of the table in FIG. 7a;

FIG. 8a is a table illustrating k2-values and original k-values computed for different electrical current distributions between three electrodes of different sizes;

FIG. 8b is a diagram of the computed k2-values and original k-values of the table in FIG. 8a;

FIG. 9a is a table illustrating weighting values for the electrodes used to compute a k2-value; and FIG. 9b is a table illustrating weighting values for the electrodes used to compute another k2-value.

DETAILED DESCRIPTION

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder sublaxation, headache, etc.

Figure 1:
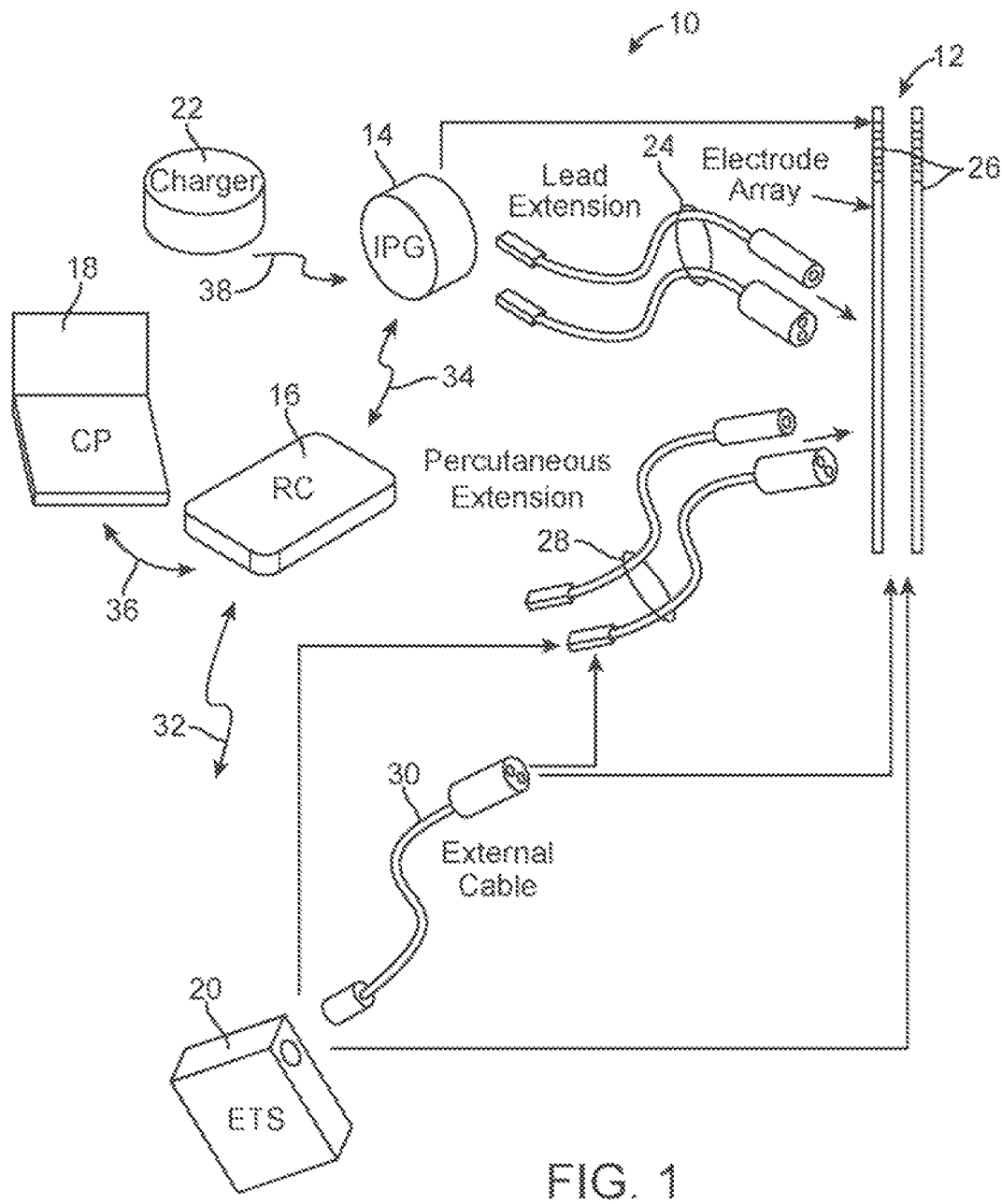
FIG. 1 is block diagram of a deep brain stimulation (DBS) system arranged in accordance with the present inventions.

Turning first to FIG. 1, an exemplary DBS neurostimulation system 10 generally includes at least one implantable stimulation lead 12 (in this case, two), a neurostimulator in the form of an implantable pulse generator (IPG) 14, an external remote controller RC 16, a clinician's programmer (CP) 18, an External Trial Stimulator (electrodes ETS) 20, and an external charger 22.

The IPG 14 is physically connected via one or more percutaneous or subdural lead extensions 24 to the neurostimulation leads 12, which carry a plurality of electrodes 26 arranged in an array. In the illustrated embodiment, the neurostimulation leads 12 are percutaneous leads, and to this end, the electrodes 26 may be arranged in-line along the neurostimulation leads 12. In alternative embodiments, the electrodes 26 may be arranged in a two-dimensional pattern on a single paddle lead if cortical brain stimulation is desired, or in a non-linear fashion about the lead, as in e.g. directional leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous or subdural lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein.

For the purposes of brevity, the details of the RC 16, ETS 20, and external charger 22 are described in U.S. Pat. No. 6,895,280, which is expressly incorporated herein by reference.

Figure 2:
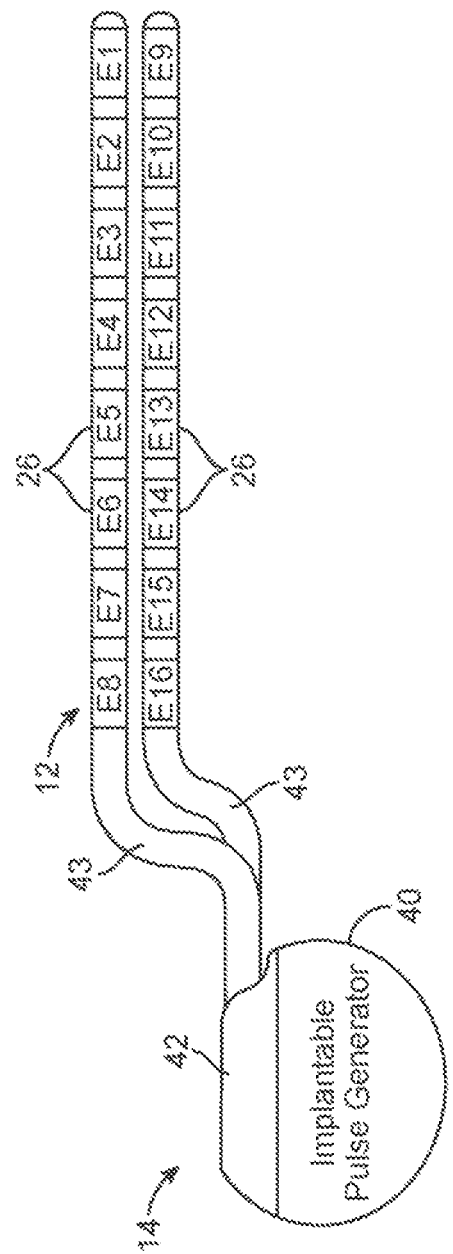
FIG. 2 is a plan view of an implantable pulse generator (IPG) and two percutaneous neurostimulation leads used in the DBS system of FIG. 1.

Referring to FIG. 2, the IPG 14 comprises an outer case 40 for housing the electronic and other components (described in further detail below), and a connector 42 to which the proximal end of the neurostimulation lead 12 mates in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Each of the neurostimulation leads 12 comprises an elongated cylindrical lead body 43, and the electrodes 26 take the form of ring electrodes mounted around the lead body 43. One of the neurostimulation leads 12 has eight electrodes 26 (labeled E1-E8), and the other stimulation lead 12 has eight electrodes 26 (labeled E9-E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 includes a battery and pulse generation circuitry (not shown) that delivers the electrical stimulation energy in the form of a pulsed electrical waveform to the electrode array 26 in accordance with a set of stimulation parameters programmed into the IPG 14. Such stimulation parameters may comprise electrode sets, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y). The IPG 14 may be capable of delivering the stimulation energy to the electrode array 26 over multiple channels or over only a single channel.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Tripolar stimulation occurs when three of the lead electrodes 26 are activated, two as anodes and the remaining one as a cathode, or two as cathodes and the remaining one as an anode.

In the illustrated embodiment, the IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention.

The IPG 14 includes a Coulomb counter (not shown) that measures the delivery of charge to the tissue region by the electrodes 26 in Coulombs. The Coulomb counter is used to measure or calculate the quantity of charge flowing into the tissue region to thereby provide rates of the charging of the tissue. In particular, the Coulomb counter may determine the amount of tissue charge at the electrodes 26 by measuring a voltage drop across a low impedance series resistance on the neurostimulation lead(s) 12.

Alternatively, rather than monitoring the amount of tissue charge, the IPG 14 or the CP 18 may be able to generate an estimate of an amount of tissue charge at each of the electrodes 26 based on the stimulation parameters that are programmed for the electrodes 26. In particular, the amount of charge actually delivered in a stimulation pulse is related to the characteristics of the stimulation pulse.

When the pulse amplitude characterizes the current amplitude of the stimulation pulses in the stimulus waveform, the amount of charge actually delivered can be estimated in accordance with the following equation: [2] $Q \approx (PA)(PD)$, where Q is the delivered charge, PA is the pulse amplitude, and PD is the pulse duration. Equation [1] can be adjusted to accommodate various forms of pulse amplitude. For example, when the pulse amplitude changes over time, Equation [1] can be changed to a time integral that includes the changing pulse amplitude.

Conversely, when the pulse amplitude characterizes the voltage amplitude of the stimulation pulses in the stimulus waveform, the amount of charge actually delivered (Q) can be estimated in accordance with the following equation: [3] $Q \approx (PA)(PD)/Z$, where Q is the delivered charge, PA is the pulse amplitude, PD is the pulse duration, and Z is the electrical impedance of current flow from one electrode 26 through the tissue to another electrode 26. Electrical impedance can vary over time with changes in the electrodes 26 and/or surrounding tissue. For example, the location of an electrode 26 within a moving body can vary over time, the electrical characteristics of tissue at the site of stimulation can vary over time, the electrode 26 itself can become contaminated (e.g., biofouling) or otherwise change over time, or the electrode-electrolyte interface can vary over time.

The impedance Z can be determined repeatedly during the operation of the neurostimulation system 10. Alternatively, the impedance Z can be estimated and programmed into the system 10. Equation [2] can be adjusted to accommodate various forms of pulse amplitude and impedance Z. For example, when the pulse amplitude and/or impedance Z changes over time, Equation [2] can be changed to a time integral that includes the changing pulse amplitude and/or impedance Z. Further details discussing the estimating of the tissue charge at each of the electrodes 26 are disclosed in U.S. Pat. No. 7,801,600, which is expressly incorporated herein by reference. Further details discussing the detailed structure and function of IPGs are described more fully in U.S. Pat. Nos. 6,516,227 and 6,993,384, which are expressly incorporated herein by reference.

Figure 3:
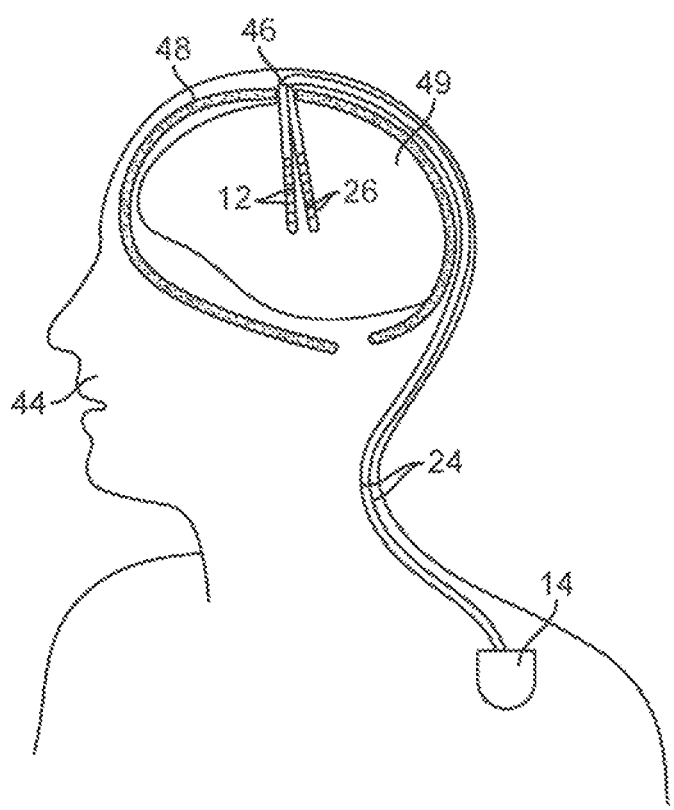
FIG. 3 is a plan view of the DBS system of FIG. 1 in use with a patient.

As shown in FIG. 3, two percutaneous neurostimulation leads 12 are introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

As briefly discussed above, the CP 18 greatly simplifies the programming of multiple electrode sets, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 in the brain.

The overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

Figure 4:
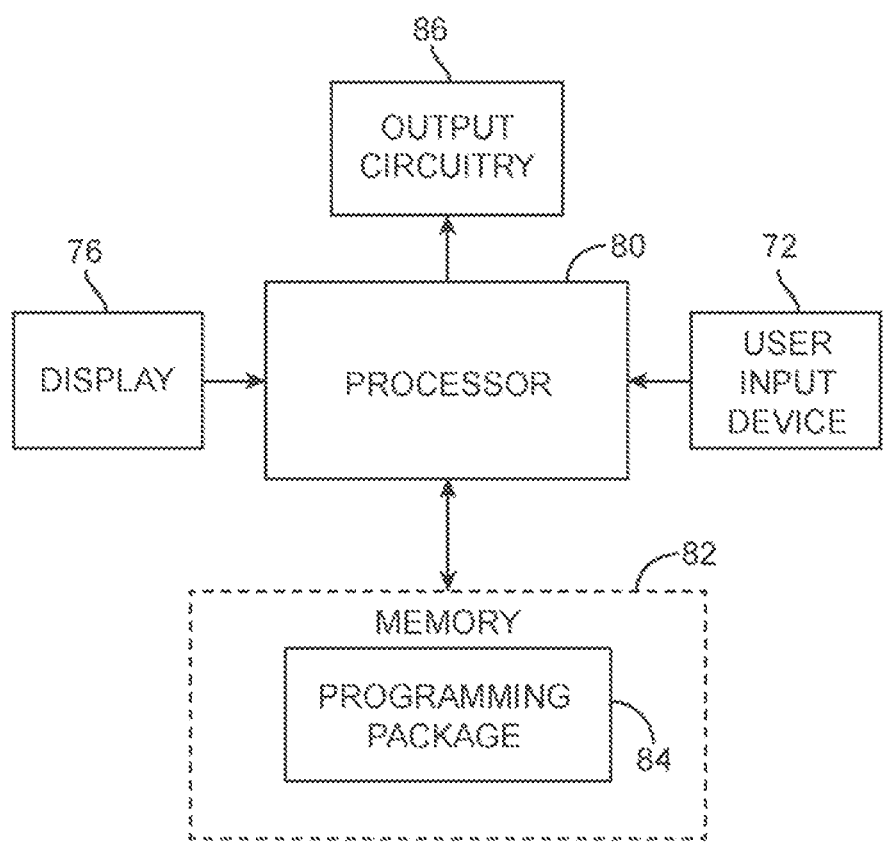
FIG. 4 is a block diagram of the internal components of a clinician's programmer (CP) used in the DBS system of FIG. 1.

Referring to FIG. 4, to allow the user to perform these functions, the CP 18 includes a standard user input device 72 (e.g., a keyboard, mouse, joystick, etc.) to allow a clinician to input information and control the process and a display monitor 76 housed in a case. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch. The CP 18 generally includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16. Notably, while the controller/processor 80 is shown in FIG. 4 as a single device, the processing functions and controlling functions can be performed by a separate controller and processor.

Execution of the programming package 84 by the controller/processor 80 provides a multitude of display screens (not shown) that can be navigated through via the user input device 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a therapy-relevant map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

As discussed in the background, there are limits as to how much charge (both in terms of total charge per pulse (or phase) and charge density per pulse) can be injected into tissue without causing any tissue damage or can be applied to the electrodes without causing any electrochemical damage (i.e. corrosion) to the electrodes. To prevent any possible tissue damage or electrode damage from occurring, the controller/processor 80 is configured for computing a charge injection metric value in response to input from the user that modifies a set of stimulation parameters (e.g., if the user attempts to increase the amplitude of the stimulation energy to the electrodes 26 or steers electrical current between the electrodes 26), comparing the computed charge injection metric value to a safety threshold value, and performing a corrective action based on the comparison.

In the illustrated embodiment, the charge injection metric value is computed based on a monitored injection charge of the currently delivered electrical energy (e.g., using the Coulomb counter contained in the IPG 14). However, in certain embodiments, the tissue charge injection metric value can be computed by the CP 18 or the IPG 14 based on a charge value estimated from a stimulation parameter or parameters selected by the user (e.g., using equations [1] or [2]), so that the electrical energy need not be monitored.

The corrective action may, e.g., comprise preventing the IPG 14 from delivering the electrical stimulation energy to the electrodes 26. For example, the IPG 14 In this case, the threshold value may define a hard stop limit. Or the corrective action may, e.g., comprise delivering the electrical stimulation energy to the electrodes 26 in accordance with a different set of stimulation parameters. The different set of stimulation parameters may be the current set of stimulation parameters in accordance with which electrical stimulation energy was delivered to the patient prior to the last user input. Or, the different set of stimulation parameters may be computed using a heuristic set of rules that ensures that the charge injection metric value does not exceed the safety threshold value.

In the case where the user input is steering current, e.g., in accordance with current steering algorithms discussed in U.S. Pat. No. 6,052,624, the different set of stimulation parameters may be a different fractionalized electrode combination. For example, the electrical stimulation energy may be steered along the tissue region by first incrementally shifting electrical current from a first electrode to a second electrode. When the charge injection metric value breaches the safety threshold value, the electrical current may be incrementally shifting from the first electrode to a third electrode. In the cases where electrical stimulation energy is prevented from being delivered to the active electrodes 26 or electrical stimulation energy is delivered to the active electrodes 26 in accordance with a different set of stimulation parameters, the safety threshold value may take the form of a hard stop limit.

Or the corrective action may be conveying a user-discernible warning signal to the user (e.g., a binary signal, such as a visual signal, an aural signal, a vibratory signal, and a modulated neurostimulation signal) or a user-discernible notification message to the user. In this case, the threshold value may define a warning threshold.

In the illustrated embodiment, the hard stop limits and/or warning thresholds are user-programmable to allow the user the flexibility of modifying them from the manufacturer set hard stop limits, which are typically selected to be at the upper threshold of the tissue safety limit and, as such, can sometimes be dangerously close for a physician's comfort level. In alternative embodiments, the IPG 14 may automatically detect the type of neurostimulation leads coupled to it (and thus, the characteristics (e.g., size, shape, material, etc.) of the electrodes carried by the leads), which information could be used by either the IPG 14 or the CP 18 to automatically modify the hard stop limits and/or warning thresholds. In this manner, the user will not have to guess or otherwise take the time to determine what the values of the hard stop limits and/or warning thresholds should be.

The hard stop limits and/or warning thresholds for the electrodes may be programmable by the user into the system 10 through means of a numerical textual entry, up/down arrow push buttons, a touch screen interface, and/or a user audio interface located on the CP 18. In particular, the CP 18 includes a programming screen that enables the user to program their desired stimulation hard stop limit values and/or warning threshold values into the neurostimulation system. This feature is useful if the user would like to be warned of the occurrence of a specific stimulation level when it is reached, or if the user would like to program the electrode(s) to not meet or exceed a specific stimulation level. Further details discussing programmable hard stop limits and/or warning thresholds are disclosed in U.S. patent application Ser. No. 13/470,158, entitled "Management of Stimulation Safety Limits in a Neurostimulation System," which is expressly incorporated herein by reference.

It can be appreciated that the manner in which the neurostimulation system 10 controls the tissue charge injection based on the hard stop limit and/or the warning threshold will depend on where the tissue charge injection is monitored or estimated and where the monitored or estimated tissue charge injection is compared to the hard stop limit and/or the warning threshold.

In the illustrated embodiment, the CP 18 both estimates the tissue charge injection at the active electrodes 26 and performs the corrective action. In particular, the CP 18 computes an estimate of the tissue charge injection the active electrodes 26 based on the programmed stimulation parameters, derives the charge injection metric value from the tissue charge injection data obtained or estimated by the IPG 14 or CP 18, and determines whether the derived charge injection metric value breaches the hard stop limit and/or the warning threshold. If the CP 18 determines that the charge injection metric value breaches the hard stop limit and/or warning threshold, the CP 18 performs the corrective action or instructs the IPG 14 to perform the corrective action.

Alternatively, the IPG 14 both monitors or estimates the tissue charge injection at the active electrodes and performs any corrective action. In particular, the IPG 14 obtains the tissue charge injection data from the active electrodes 26 or computes an estimate of the tissue charge injection data based on the programmed stimulation parameters, derives the charge injection metric value from the obtained or estimated tissue charge injection data, and determines whether the derived charge injection metric value breaches the hard stop limit and/or the warning threshold. If the IPG 14 determines that the charge injection metric value breaches the hard stop limit and/or warning threshold, the IPG 14 performs the corrective action or instructs the CP 18 to perform the corrective action.

Alternatively, the IPG 14 monitors or estimates the tissue charge injection at the active electrodes 26, while the CP 18 performs the corrective action if needed. In particular, the IPG 14 obtains the tissue charge injection data from the active electrodes 26 or computes an estimate of the tissue charge injection data based on the programmed stimulation parameters, and sends the tissue charge injection data to the CP 18, which derives the charge injection metric value from the obtained or estimated tissue charge injection data, and determines whether the derived injection metric value breaches the hard stop limit and/or the warning threshold. If the CP 18 determines that the charge injection metric value breaches the hard stop limit and/or the warning threshold, the CP 18 performs the corrective action or instructs the IPG 14 to perform the corrective action.

More alternatively, the CP 18 estimates the tissue charge injection at the electrodes 26, and the IPG 14 performs the corrective action. In particular, the CP 18 computes an estimate of the tissue charge injection at the electrodes 26 based on the programmed stimulation parameters, and sends the tissue charge injection data to the IPG 14. The IPG 14 receives the estimated tissue charge injection data from the CP 18, derives the charge injection metric value from the estimated tissue charge injection data, and determines whether the derived charge injection metric value has met or exceeded the hard stop limit and/or the warning threshold. If the IPG 14 determines that the charge injection metric value breaches the hard stop limit and/or warning threshold, the IPG 14 performs the corrective action or instructs the CP 18 to perform the corrective action.

Significantly, much like the original k-value, the charge injection metric value is a function of a physical electrode parameter (e.g., electrode surface area, electrode surface shape, or an electrode material) and an electrical source parameter (e.g., current, voltage, charge, charge density, and impedance). However, unlike the original k-value, the charge injection metric value is computed for multiple electrodes at one time, rather than being computed on an electrode-by-electrode basis. In the embodiment illustrated herein, the charge injection metric value considers the electrode surface area and charge for distinct electrodes as independent contributors to a final "k" value, described as "k2" in the following equation:

$$k2 = \log_{10}\left(\sum_{i=1}^{n} \frac{Q_i^2}{A_i}\right), \quad [4]$$

where i is an electrode designator, n is the number of electrodes, $Q_i$ is the charge injected by the electrode i, and $A_i$ is the surface area of the electrode i.

It should be noted that under certain conditions, the k2 model reduces to the original Shannon model provided by equation [1]. In particular, in the cases where only a single electrode is considered or when multiple electrodes where the fraction of the current through a given electrode is equal to the fraction of the total surface area that the electrode provides (e.g., if 50% of the current is going through an electrode that provides 50% of the total surface area, then the k2-value is equivalent to k-value where A equals the total surface area and Q equals the total charge), the k2 model reduces to the original Shannon model.

Simplification of the k2 model to the original Shannon model in the case of multiple electrodes can be described in the following proof. If the surface area A is divided into n segments of arbitrary size—denoted as fractions of the total surface area ($f_1, f_2, \ldots, f_n$), such that $f_1+f_2+ \ldots +f_n=1$. If $Q_i=f_iQ$, and $A_i=f_iA$, it follows that:

$$\frac{Q_i^2}{A_i} = \frac{(f_iQ)^2}{f_iA} = \frac{f_i^2Q^2}{f_iA} = f_i\frac{Q^2}{A}.$$

By substitution, $$k2 = \log_{10}\left(\sum_{i=1}^{n} f_i \frac{Q^2}{A}\right) = \log_{10}\left(\left(\sum_{i=1}^{n} f_i\right)\frac{Q^2}{A}\right),$$

and given that $$\left(\sum_{i=1}^{n} fi\right) = 1, \text{ then } k2 = \log_{10}\left(\frac{Q^2}{A}\right)$$

It should be noted that for a given k-value threshold, the k2 model is conservative compared to the existing approach of evaluating the charge limit on an electrode-by-electrode basis. That is, the k2 model cannot allow the original k-value on any one electrode (assuming an electrode-by-electrode assessment approach) to breach the original k-value threshold. That is not possible because in the k2 model, each active electrode (of a given polarity) counts against the total permissible k.

Having described the general concept of the k2 model, several examples that illustrate how the k2-value changes as current is distributed among electrodes, and highlight the scenarios in which the k2 model reduces to the original Shannon model will now be described.

Figures 5A, 5B:
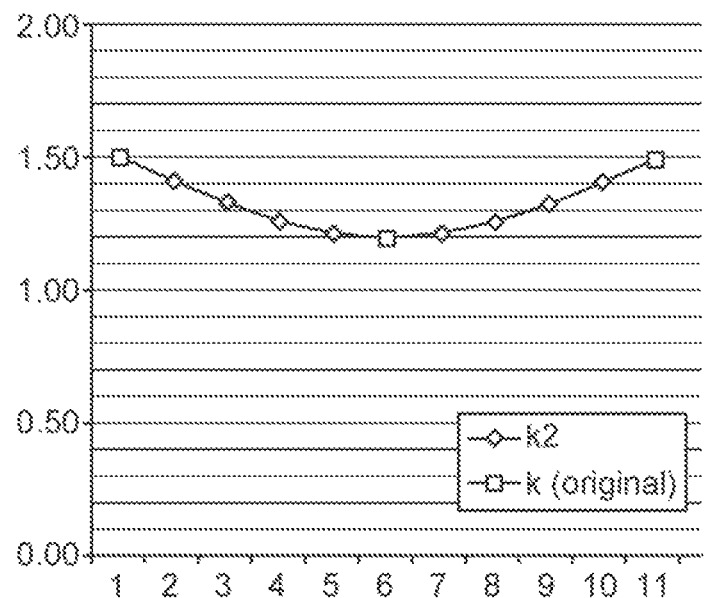

In the first example illustrated in FIGS. 5a and 5b, the split between two electrodes (e1 and e2) of the same size is varied. As can be seen, the k2-value is highest when electrical current is concentrated on a single electrode (i.e., 100%-0% or 0%-100% for electrodes e1 and e2, respectively), and lowest when electrical current is evenly distributed between electrodes e1 and e2 (50%-50% for electrodes e1 and e2, respectively). For electrical current splits that can be reduced to scenarios that fit the original Shannon model (100%-0%, 50%-50%, 0%-100% for electrodes e1 and e2, respectively), the original k-value and k2-value are the same, which exemplifies the conservative property of the k2 model.

Figures 6A, 6B:
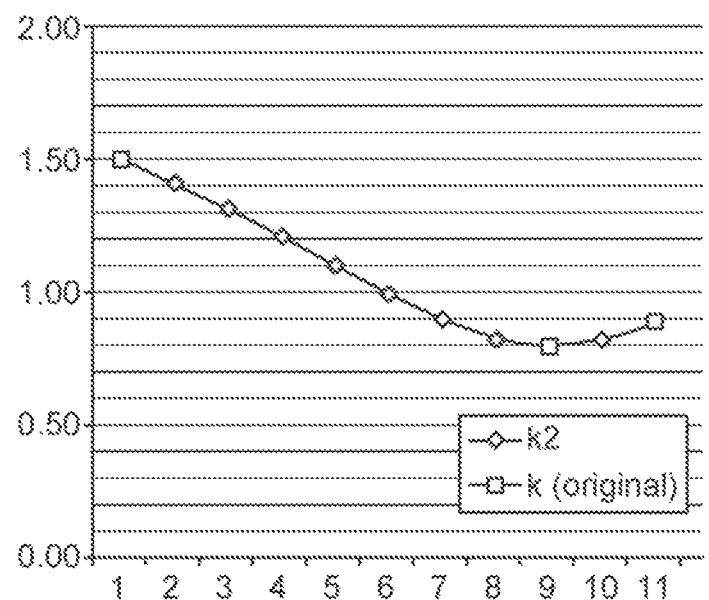

In the second example illustrated in FIGS. 6a and 6b, the split between two electrodes (e1 and e2) of different sizes (electrode e2 is four times as large as electrode e1) is varied. As can be seen, the k2-value is highest when electrical current is concentrated on the smallest electrode (100%-0% for electrodes e1 and e2, respectively), and lowest when electrical current is distributed between electrodes e1 and e2 in proportion to the surface areas of the electrodes e1 and e2 (20%-80% for electrodes e1 and e2, respectively). For electrical current splits that can be reduced to scenarios that fit the original Shannon model (100%-0%, 20%-80%, 0%-100% for electrodes e1 and e2, respectively), the original k-value and k2-value are the same, which exemplifies the conservative property of the k2 model.

Figures 7A, 7B:
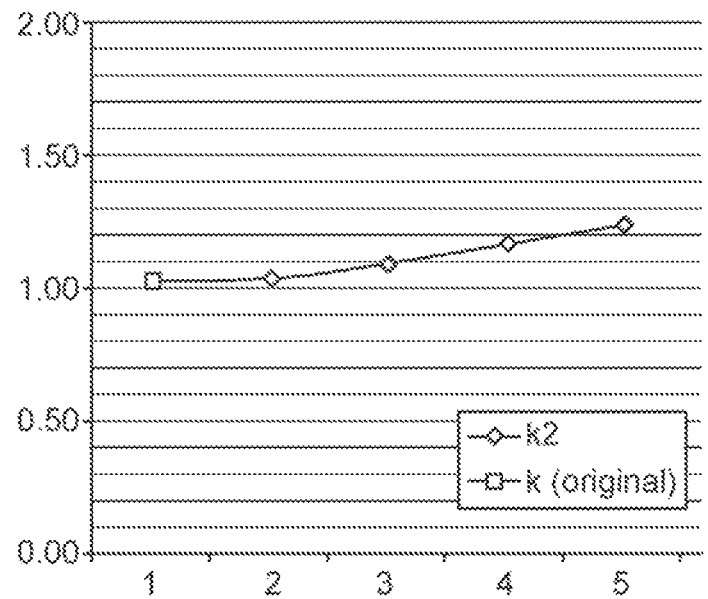

In the third example illustrated in FIGS. 7a and 7b, the split between three electrodes (e1, e2, and e3) of the same size is varied. As can be seen, the k2-value is highest when the electrical current is most concentrated (67%-33%-0% for electrodes e1, e2, and e3, respectively), and lowest when the electrical current is most distributed (33%-33%-33% for electrodes e1, e2, and e3, respectively). For electrical current splits that can be reduced to scenarios that fit the original Shannon model (33%-33%-33% for electrodes e1, e2, and e3, respectively), the original k-value and k2-value are the same, which exemplifies the conservative property of the k2 model.

Figures 8A, 8B:
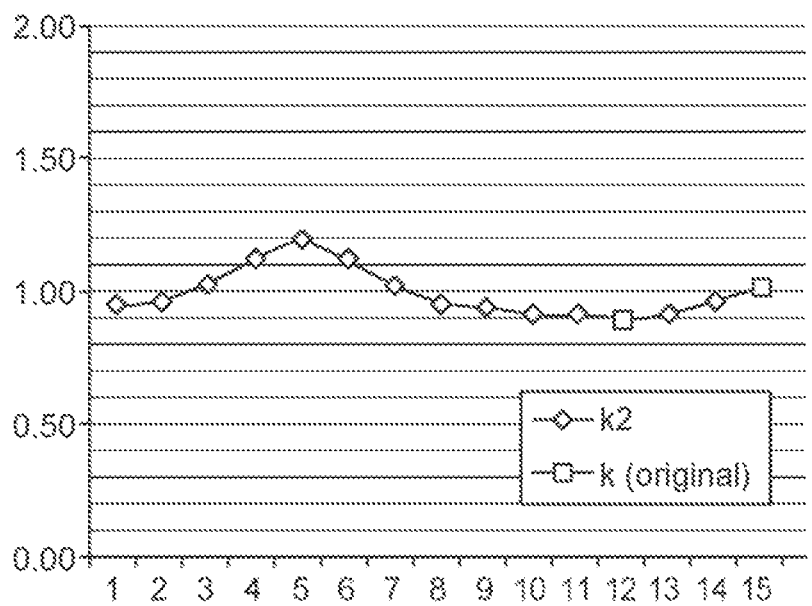

In the fourth example illustrated in FIGS. 8a and 8b, the split between three electrodes (e1, e2, and e3) of different sizes (electrode e1 is twice as large as electrodes e2 and e3) is varied. As can be seen, the k2-value is highest when the electrical current is most concentrated on the smallest electrode (33%-67%-0% for electrodes e1, e2, and e3, respectively), and lowest when the electrical current is distributed between electrodes e1, e2, and e3 in proportion to the surface areas of the electrodes e1, e2, and e3. For electrical current splits that can be reduced to scenarios that fit the original Shannon model (50%-25%-25% or 67%-33%-0% for electrodes e1, e2, and e3, respectively), the original k-value and k2-value are the same, which exemplifies the conservative property of the k2 model.

The foregoing examples suggest that the k2 model is a conservative, yet reasonable approach for managing charge injection with multiple electrodes and multiple electrical sources. It should be noted that equation [4] treats the charge at each active electrode equally. However, each of the active electrodes may be weighted to take into account unequal contributions of the active electrodes on the k2-value. In particular, the k2-value of the active electrodes can be computed in accordance with the following equation:

$$k2 = \log_{10}\left(\sum_{i=1}^{n} W_i \frac{Q_i^2}{A_i}\right), \quad [5]$$

where k2 is the tissue charge injection safety value, i is an electrode designator, n is the number of electrodes, $Q_i$ is the charge injected by the electrode i, $A_i$ is the surface area of the electrode i, and Wi is a weighting for the electrode i. The weighting values $W_i$ may be hard-coded into the system or may be programmable by the user.

In one embodiment, the weighting values $W_i$ for the respective electrodes are determined based on the adjacency or proximity of electrodes to each other. In particular, equation [4] does not take the relative spatial location of multiple active electrodes into account, and could be excessively conservative when the active electrodes are far apart, and most applicable when the active electrodes are tightly juxtaposed. However, equation [5] can be used take the relative spatial location of the multiple active electrodes into account. For example, the weighting value $W_i$ for a particular electrode may be an adjacency weighting that may be relatively high if it is relatively close to a reference electrode or relatively low (or zero) if it is relatively far away from the reference electrode.

In one embodiment, the adjacent weighting value $W_i$ may be binary (i.e., only two values are available), such that an active electrode that is relatively far away from the reference electrode may be equal to 0, and an active electrode that is relatively close to the reference electrode may be equal to 1. Thus, the active electrodes having weighting values $W_i$ of 0 do not affect the k2-value computed for the active electrodes having weighting values $W_i$ of 1. In another embodiment, the weighting value $W_i$ may be graduated from 0 to 1 in increments of, e.g., 0.1, in accordance with the proximity of the respective electrode from a reference electrode. Active electrodes that are deemed to be relatively far away from the reference electrode may be assigned a weighting of 0, whereas the remaining electrodes may be assigned a non-zero weighting. For example, as illustrated in FIG. 9a, electrodes e1-e5 are assigned non-zero weighting values $W_i$ (with electrode e3 being the reference electrode, and therefore, assigned a weighting of 1), whereas electrodes e6-e8 are assigned zero weighting values $W_i$ due to their relatively far proximity to reference electrode e3. Thus, electrodes e6-e8 do not affect the k2-value computed for electrodes e1-e5.

The concept of adjacency weightings $W_i$ may be extended to neurostimulation leads. For example, the electrodes carried by one neurostimulation lead can be uniformly weighted based on the proximity of that neurostimulation lead to a reference neurostimulation lead. The CP 18 may have a toggle switch that can be actuated to alternately deem two neurostimulation leads to be relatively close to each other, in which case, the weighting values $W_i$ for all the active electrodes will be 1, or deem the two neurostimulation leads to be relatively far away from each other, in which case, the weighting values $W_i$ for all the electrodes carried by the neurostimulation lead of interest will be 1, whereas the weighting values $W_i$ for all the electrodes carried by the other neurostimulation lead will be 0.

Notably, several k2-values may be computed for different combinations of the active electrodes. For example, in the case where the weighting values $W_i$ are binary, any of the active electrodes that have been assigned a weighting value $W_i$ of 0, may be selected as a reference electrode for determining adjacencies for other ones of the active electrodes. For example, a first k-value ($k2_a$) may be computed for electrodes e1-e5, as previously discussed with respect to FIG. 9a, and a second k2-value ($k2_b$) can be computed for electrodes e6-e8, which were assigned a weighting value $W_i$ of 0 in FIG. 9a. As shown in FIG. 9b, electrodes e6-e8 are assigned non-zero weightings (with electrode e7 being the reference electrode, and therefore, assigning a weighting of 1), whereas electrodes e1-e5 are assigned zero weightings due to their relatively far proximity to reference electrode e7. Thus, two k2-values are respectively computed for electrodes e1-e5 and electrodes e6-e8. For cases where multiple k2-values are computed, a function (e.g., a maximum, a sum, an average, or a minimum) of these k2-values will be compared to the safety threshold value (e.g., a hardstop limit and/or a warning threshold), and a corrective action will be performed if the function of the k2-values breach the safety threshold value.

In the case where the weighting values Ware graduated, the total number of k2-values computed may be equal to the total number of active electrodes, with each k2-value being associated with a combination of electrodes having a different reference electrode. That is, one of the active electrodes can be selected as a reference electrode, and the remaining electrodes can be assigned weighting values $W_i$ in accordance to their proximities to the reference electrode; then, a different active electrode can be selected as a reference electrode, and the remaining electrodes can be assigned weighting values $W_i$ in accordance to their proximities to the new reference electrodes; and so on.

Although the weighting values $W_i$ have been described with respect to electrode proximity, it should be noted that the weighting values $W_i$ can be applied to other variable aspects of the electrodes or nature of electrical current delivered to the electrodes. For example, active electrodes that deliver cathodic electrical current may be weighted differently from active electrodes that deliver anodic electrical current. In one embodiment, when computing a k2-value, active cathodic electrodes may be assigned a weighting value W; of 1.0, whereas active anodic electrodes may be assigned a weighting value W; of 0.4. Alternatively, active anodic electrodes may not be considered at all when computing the k2-value, in which case, they may be assigned a weighting value $W_i$ of 0.

In an optional embodiment, a computed k2-value or a safety threshold value may be scaled up or down to create a final k2-value or final safety threshold value prior to comparison. In one embodiment, the safety threshold value may take the form of a discrete function of the frequency of the electrical current. For example, the safety threshold value may be equal to 5 for frequencies in the range of 0 Hz to 100 Hz, and equal to 3 for frequencies above 100 Hz. In another embodiment, the safety threshold value may be a continuous function of the frequency of the electrode electrical. For example, the safety threshold value may be computed in accordance with either of the following equations: k2=m*F+b, or k2=a*F$^2$+b*F+c, where a, b, c, and m are constants, and F is the frequency of the electrical current.

In other embodiments, a plurality of different safety threshold values may be stored in memory, one of which can be selected based on a characteristic shared by the active electrodes for which the k2-value will be computed. For example, the stored safety threshold values may be respectively associated with different frequencies, in which case, the safety threshold value associated with the frequency of the electrical current is delivered to the active electrodes can be selected for comparison to the computed k2-value. Or the stored safety threshold values may be respectively associated with different polarities, in which case, the safety threshold value associated with the polarity of the electrical current delivered to the active electrodes can be selected for comparison to the computed k2-value.

Although the function of computing the k2-value and performing the corrective actions has been described as being performed by the CP 18 and/or IPG 14, it should be appreciated that the RC 16 may compute the k2-value and/or perform the corrective action. Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

We claim:
1. A neurostimulation system, comprising:
   a memory having a safety threshold value stored in the memory; and
   a processor coupled to the memory and configured for
      determining or assigning a weighting value for each of at least two active electrodes based on a proximity of
         a) the at least two active electrodes to each other or
         b) a corresponding one of the at least two active electrodes to a reference electrode;
      computing, for a set of stimulation parameters, a charge injection metric value as a function of at least two parameters and the weighting value for each of the at least two active electrodes;
      comparing the computed charge injection metric value to the safety threshold value; and
      performing a corrective action based on the comparison when the computed charge injection metric value exceeds the safety threshold value.

2. The neurostimulation system of claim 1, wherein the at least two parameters comprises a physical electrode parameter and an electrical source parameter.

3. The neurostimulation system of claim 2, wherein the physical electrode parameter is at least one of an electrode surface area, an electrode surface shape, or an electrode material.

4. The neurostimulation system of claim 2, wherein the electrical source parameter is at least one of a current, a voltage, a charge, charge density, or an impedance.

5. The neurostimulation system of claim 1, wherein the weighting value for at least one of the at least two active electrodes varies inversely with distance from the reference electrode.

6. The neurostimulation system of claim 1, wherein the weighting value for at least one of the at least two active electrodes varies inversely with distance from another one of the at least two active electrodes.

7. The neurostimulation system of claim 1, wherein performing the corrective action comprises conveying a warning signal to a user.

8. The neurostimulation system of claim 1, wherein performing the corrective action comprises preventing delivery of electrical stimulation energy to the at least two active electrodes using the set of stimulation parameters.

9. The neurostimulation system of claim 1, wherein performing the corrective action comprises delivering electrical stimulation energy to the at least two active electrodes in accordance with a different set of stimulation parameters.

10. The neurostimulation system of claim 1, further comprising an implantable pulse generator comprising the processor.

11. The neurostimulation system of claim 1, further comprising a programmer comprising the processor.

12. A neurostimulation system, comprising:
a memory having a warning threshold value and a hard stop limit stored in the memory; and
a processor coupled to the memory and configured for
determining or assigning a weighting value for each of at least two active electrodes based on a proximity of a) the at least two active electrodes to each other or b) a corresponding one of the at least two active electrodes to a reference electrode;
determining, for a set of stimulation parameters, a charge injection metric value as a function of at least two parameters and the weighting value for each of the at least two active electrodes;
comparing the charge injection metric value to the warning threshold value and conveying a warning signal to a user when the charge injection metric value exceeds the warning threshold value;
comparing the charge injection metric value to the hard stop limit; and
performing a corrective action when the charge injection metric value exceeds the hard stop limit.

13. The neurostimulation system of claim 12, wherein performing the corrective action comprises preventing delivery of electrical stimulation energy to the at least two active electrodes using the set of stimulation parameters.

14. The neurostimulation system of claim 12, wherein performing the corrective action comprises delivering electrical stimulation energy to the at least two active electrodes in accordance with a different set of stimulation parameters.

15. The neurostimulation system of claim 12, wherein determining the charge injection metric value comprises computing the charge injection metric value.

16. The neurostimulation system of claim 15, wherein computing the charge injection metric value comprises computing the charge injection metric value as a function of a physical electrode parameter and an electrical source parameter.

17. The neurostimulation system of claim 16, wherein the physical electrode parameter is at least one of an electrode surface area, an electrode surface shape, or an electrode material.

18. The neurostimulation system of claim 16, wherein the electrical source parameter is at least one of a current, a voltage, a charge, charge density, or an impedance.

19. A method of operating a neurostimulation system, the method comprising:
determining or assigning a weighting value for each of at least two active electrodes based on a proximity of a) the at least two active electrodes to each other or b) a corresponding one of the at least two active electrodes to a reference electrode;
determining, for a set of stimulation parameters, a charge injection metric value as a function of at least two parameters and the weighting value for each of the at least two active electrodes;
comparing the charge injection metric value to a warning threshold value and conveying a warning signal to a user when the charge injection metric value exceeds the warning threshold value;
comparing the charge injection metric value to a hard stop limit; and
performing a corrective action when the charge injection metric value exceeds the hard stop limit.

20. The method of claim 19, further comprising receiving the warning threshold value or the hard stop limit.

* * * * *